(12) United States Patent
Bjornstad et al.

(10) Patent No.: US 10,711,040 B2
(45) Date of Patent: Jul. 14, 2020

(54) LOW SUBSTITUTED POLYMYXINS AND COMPOSITIONS THEREOF

(71) Applicant: XELLIA PHARMACEUTICALS APS, Copenhagen S (DK)

(72) Inventors: Vidar Bjornstad, Oslo (NO); Solvi Gunnes, Lommedalen (NO); Torben Koch, Copenhagen NV (DK); Claes Melander, Malmo (SE)

(73) Assignee: XELLIA PHARMACEUTICALS APS, Copenhagen (DK)

( * ) Notice: Subject to any disclaimer, the term of this patent is extended or adjusted under 35 U.S.C. 154(b) by 0 days.

(21) Appl. No.: 15/324,882

(22) PCT Filed: Jun. 29, 2015

(86) PCT No.: PCT/EP2015/064764
§ 371 (c)(1),
(2) Date: Jan. 9, 2017

(87) PCT Pub. No.: WO2016/005223
PCT Pub. Date: Jan. 14, 2016

(65) Prior Publication Data
US 2017/0218024 A1    Aug. 3, 2017

Related U.S. Application Data

(60) Provisional application No. 62/022,399, filed on Jul. 9, 2014.

(51) Int. Cl.
*C07K 7/62* (2006.01)
*A61K 38/00* (2006.01)

(52) U.S. Cl.
CPC ............... *C07K 7/62* (2013.01); *A61K 38/00* (2013.01); *Y02A 50/473* (2018.01)

(58) Field of Classification Search
CPC ..................................................... C07K 7/62
See application file for complete search history.

(56) References Cited

U.S. PATENT DOCUMENTS

| | | | |
|---|---|---|---|
| 3,317,506 A | 5/1967 | Wilkinson | |
| 5,767,068 A * | 6/1998 | VanDevanter | A61K 38/12 424/499 |
| 2003/0143162 A1 | 7/2003 | Speirs et al. | |
| 2004/0022740 A1 | 2/2004 | Baker et al. | |
| 2008/0066739 A1 | 3/2008 | Lemahieu et al. | |
| 2012/0316105 A1 | 12/2012 | Magee et al. | |
| 2016/0002296 A1 | 1/2016 | Gunnes et al. | |
| 2017/0239321 A1 | 8/2017 | Bencic | |

FOREIGN PATENT DOCUMENTS

| | | |
|---|---|---|
| DE | 1906699 A1 | 2/1970 |
| EP | 1752161 A2 | 2/2007 |
| FR | 1586834 A | 3/1970 |
| RU | 2712276 C2 | 1/2020 |
| WO | 19890009626 A1 | 10/1989 |
| WO | 199820836 | 5/1998 |
| WO | 2008025560 A1 | 3/2008 |
| WO | 2011051070 A1 | 5/2011 |
| WO | 2012168820 A1 | 12/2012 |
| WO | 2014108469 A1 | 7/2014 |
| WO | 2014195405 A1 | 12/2014 |

OTHER PUBLICATIONS

Kassamali (Polymyxins: Wisdom Does Not Always Come With Age, Clinical Infectious Diseases 2013, 57:877-83) (Year: 2013).*
Kassamali et al. "Polymixins: Wisdom Does Not Always Come With Age", Healthcare Epidemiology, 2013; pp. 877-883 (Year: 2013).*
European Medicines Agency Assessment report of polymixin-based products, EMA/CHMP/153652/2015, dated Feb. 26, 2015.
Suter et al.; "The Sulfomethylation Reaction"; J. Org. Chem.; 10(5); pp. 470-478; (1945).
Bergen et al.; "Colistin Methanesulfonate Is an Inactive Prodrug of Colistin Against Pseudomonas Aeruginosa"; Antimicrobial Agents and Chemotherapy; pp. 1953-1958; (2006).
He et al.; "Pharmacokinetics of Four Different Brands of Colistimethate and Formed Colistin in Rats"; J Antimicrob Chemother; 68; pp. 2311-2317; (2013).
Healan et al.; "Stability of Colistimethate Sodium in Aqueous Solution"; aac.asm.org; 56(12); pp. 6432-6433; (2012); downloaded Mar. 23, 2017 http://aac.asm.org.
Kamin et al.; "Inhalation Solutions—which one are allowed to be mixed? Physico-chemical Coompatibility of Drug Solutions in Nebulizers"; Journal of Cystic Fibrosis; 5; pp. 205-213; (2006).
Li et al; "Defining the Dosage Units for Colistin Methanesulfonate: Urgent Need for International Harmonization"; Antimicrobial Agents and Chemotherapy; 50(12); pp. 4231-4232; (2006).
Magee et al.; "Discovery of Dap-3 Polymyxin Analogues for the Treatment of Multidrug-Resistant Gram-Negative Nosocomial Infections"; Journal of Medicinal Chemistry; 53(12); pp. 5079-5093; (2013).
Shorin et al. "Antibacterial Activity, Toxicity and Medicinal Properties of Monomycin and Colimycin Methanesulfonates" Database CA [on-line]Chemical Abstracts Service, Columbus, Ohio, Database accession No. 56:38870; 4 pages (1961).
Storm et al.; "Polymyxin and Related Peptide Antibiotics"; Annual Review of Biochemistry; 46; pp. 723-763; (1977).
Van den Bossche et al.; "Identification of Impurities in Polymyxin B and Colistin Bulk Sample Using LiquidChromatography Coupled to Mass Spectrometry"; Talanta; 83; pp. 1521-1529; (2011).
Wallace et al.; "Self-assembly Behaviour of Colistin and its Prodrug Colistin Methanesulfonate: Implications for Solution Stability and Solubilization"; J. Phys Chem B., Author Manuscript: 114(14); pp. 4836-4840; (2010).
Wallace et al.; "Stability of Colistin Methanesulfonate in Pharmaceutical Products and Solutions for Administration to Patients"; Antimicrobial Agents and Chemotherapy; pp. 3047-3051; (2008).
Wishart et al.; "1 H, 13C and 15N Chemical Shift Referencing in Biomolecular NMR"; Journal of Biomolecular NMR; 6; pp. 135-140; (1995).
Young et al.; "Optimization of Anti-Pseudomonal Antibiotics for Cystic Fibrosis Pulmonary Exacerbations: IV. Colistimethate Sodium"; Pediatric Pulmonology; 48; pp. 1-7; (2013).

(Continued)

*Primary Examiner* — Lianko G Garyu
(74) *Attorney, Agent, or Firm* — Cantor Colburn LLP

(57) ABSTRACT

The present invention relates to novel low substituted polymyxins and compositions thereof.

8 Claims, 6 Drawing Sheets

(56) References Cited

OTHER PUBLICATIONS

European Medicines Agency: "Review Under Article 5(3) of Regulation EC(No) 726-2004; Polymyxin-based products"; retrieved from the Internet: URL:http://www.ema.europa.eu/docs/en_GB/document_library/Report/2015/05/WC500187326.pdf. Retrieved on Sep. 7, 2015.
International Search Report and Written Opinion; International Application No. PCT/EP2015/064764; International Filing Date Jun. 29, 2015; dated Sep. 25, 2015; 10 pages.
Li et al.; "Evaluation of Colistin as an Agent Against Multi-resistant Gram-negative Bacteria"; International Journal of Antimicrobial Agents; 25(1); pp. 11-25; (2005).
Li et al.; "Stability of Colistin and Colistin Methanesulfonate in Aqueous Media and Plasma as Determined by High-Performance Liquid Chromatography"; Antimicrobial Agents and Chemotherapy; 47(4); pp. 1364-1370; (2003).
McMillian et al.; "Sodium Colistimethate I: Dissociations of Aminomethanesulfonates in Aqueous Solution"; Journal of Pharmaceutical Sciences; ; 58(6); pp. 730-737; (1969).
Bossche et al.; "Identification of Impurities in Polymyxin B and Colistin Bulk Sample Using Liquid Chromatography Coupled to Mass Spectrometry"; Talanta; 82; pp. 1521-1529; (2011).
Govaerts et al.; "Mass Spectrometric Fragmentation of Cyclic Peptides Belonging to the Polymyxin and Colistin Antibiotics Studied by Ion Trap and Quadrupole/orthogonal-acceleration Time-of-flight Technology"; Rapid Communications in Mass Spectrometry; 16; pp. 823-833; (2002).
Athanassa et al.; "Pharmacokinetics of Inhaled Colistimethate Sodium (CMS) in Mechanically Ventilated Critically Ill Patients"; Intensive Care Med 38; pp. 1779-1786; (2012).
Barnett et al.; "Sodium Sulphomethyl Derivatives of Polymyxins"; Birt. J. Pharmacol, 23, pp. 552-574; (1964).
BioPharm International Editors; "Biopharmaceutical Manufacturing Using Blow-Fill-Seal Technology"; in BioPharm International; 24(7); 7 pages; (2011).
Keller et al.; "Performance Characteristics of Colistimethate Sodium Solutions (Colistin) Delivered by Jet Nebulizers Compared to the eFlow SCF Electronic Nebulizer"; North American Cystic Fibrosis Conference, St. Louis, USA, Oct. 14-17, 2004.
Brochet et al.; "Comparative Efficacy of Two Doses of Nebulized Colistimethate for the Eradication of Pseudomonas Aeruginosa in Children with Cystic Fibrosis"; Can Respir J; 14(8); pp. 473-479; (2007).
Falagas et al.; "Use of International Units When Dosing Colistin Will Help Decrease Confusion Related to Various Formulations of the Drug Around the World"; Antimicrobial Agents and Chemotherapy; pp. 2274-2275; (2006).
Colomycin: Package Leaflet: Information for the User; Power for Solution for Injection, Infusion or Inhalation Colistimethate Sodium; TEVA UK Limited; Manufacturer and site of batch release: Millmount Healthcare Ltd; Leaflet issued Jul. 2019; 2 pages.
Ratjen et al.; "Pharmacokinetics of Inhaled Colistin in Patients with Cystic Fibrosis"; Journal of AntimicrobialChemotherapy; 57(2); pp. 306-311; (2006).
UMHealth; Health Facts for you; "Nebulized Colistimethate (Coly-Mycin) or Colistin"; Produced by the University of Wisconsin Hospitals and Clinics Authority; Department of Nursing HF#5851; 5 pages; printed Nov. 11, 2019.
Coly-Mycin M Parental (Colistimethate for Injection, USP), Prescribing Information as of Feb. 2011; JHP Pharmaceuticals Ref: 300818F, 5 pages.
IN Application 201717000052, Search Report, dated Nov. 9, 2019; 5 pages.
Li et al.; "Colistin: The Re-emerging Antibiotic for Multidrug-resistant Gram-negative Bacterial Infections"; Lancet Infect Dis; 6; pp. 589-601; (2006).
Particles in Injections; printed Mar. 26, 2019; 8 pages http://www.uspbpep.com/usp32/pub/data/v32270/usp32nf27s0_c1.html.
Tawde, Suprita A.; "Particulate Matter in Injectables: Main Cause for Recalls"; J. Pharmacovigil; 3(1); e128; 3 pages; (2014).
Tobramycin Inhalation Solution; printed Mar. 22, 2019; 4 pages; http://www.uspbpep.com/usp32/pub/data/v32270/usp32nf27s)_m83766.html; 4 pages.
Yapa et al. Pulmonary and Systemic Pharmacokinetics of Inhaled and Intravenous Colistin Methanesulfonate in Cystic Fibrosis Patients: Targeting Advantage of Inhalation Administration; Antimicrobial Agents and Chemotherapy; 58(5); pp. 2570-2579; (2014).

* cited by examiner

PE1-(SM)$_2^1$

PE1-(SM)$_2^3$

PE1-(SM)₂⁵

PE1-(SM)₂⁸

PE1-(SM)$_2$$^9$

Start PE1-(SM)$_{10}$$^{1,3,5,8,9}$

After 90 min, pH 9..

Unchanged for 3 days, pH 8.0:

Unchanged for 3 days, pH 7.0:

Unchanged for 3 days, pH 6.5:

Unchanged for 3 days, pH6.0:

LOW SUBSTITUTED POLYMYXINS AND COMPOSITIONS THEREOF

CROSS REFERENCE TO RELATED APPLICATIONS

This application is a National Stage Application of PCT/EP2015/064764, filed on Jun. 29, 2015, which claims the benefit of U.S. Provisional Application No. 62/022,399, filed on Jul. 9, 2014, both of which are incorporated by reference in their entirety herein.

The present invention relates to novel low substituted polymyxins and compositions thereof.

BACKGROUND

Polymyxins were discovered in 1947 as antibiotics produced by *Bacillus polymyxa*. Polymyxins are antibiotic decapeptides containing a heptapeptide ring and a N-terminal amide coupled fatty acid. Today, two commercial Polymyxin mixtures are in clinical use; Polymyxin B and Polymyxin E (Colistin). Both mixtures comprise a variety of components as described in J Chromatogr A. 2002 Nov. 8; 976(1-2):65-78 by Goevaerts et al and in Talanta 2011 Feb. 15; 83(5):1521-9 by Van den Bossche et al. According to the European pharmacopoeia, Colistin should comprise more than 77% of Polymyxin E1, E2, E3, E1-i and E1-7MOA, but less than 10% of each of the minor components Polymyxin E3, E1-i and E1-7MOA.

Due to toxicity associated with Colistin, the mixture was improved by sulfomethylation in the 1950'ties. The sulfomethylated Colistin is called Colistimethate sodium (CMS) which has been considered to be a prodrug of Colistin. CMS is still in clinical use as a last-line treatment option for multidrug-resistant organisms such as *Pseudomonas aeruginosa, Acinetobacter baumannii, Klebsiella pneumonia* and other Gram negative pathogens. For many years, solutions of CMS have also been administered by nebulization into the lungs of patients with cystic fibrosis (CF) to manage colonization or infections caused by *P. aeruginosa*.

Today, the increasing problem with infections caused by antibiotic resistant pathogens has resulted in an increased use of products such as Colistin.

The fact that commercial CMS products contain a complex mixture of derivatives of different Polymyxins has several unfortunate consequences. The foremost of these relates to the therapeutic value of any marketed product. Since CMS may be considered a antibiotic-reservoir once injected or inhaled into the body, it is of importance that therapeutic levels of the activated compounds are reached before renal or metabolic clearance. Thus, a sulfomethylated polymyxin containing two sulfomethyl substituents only, provides a well-defined product with respect to molecular weight and charge.

An object of the present invention is therefore to provide improved polymyxin compounds and compositions useful as antimicrobial agents, and to overcome or at least mitigate the disadvantages of the prior art products.

SUMMARY OF THE INVENTION

This invention concerns polymyxins which comprise a total of two sulfomethyl groups attached to the γ-amino groups on DAB or DAP residues in the polypeptide moiety of polymyxins. These compounds and compositions thereof can be used in treatment of bacterial infections.

In one aspect, the present invention provides new polymyxins which are more water soluble than Polymyxin E and Polymyxin B. In yet another aspect, the present invention provides sulfomethylated polymyxins which are more stable in aqueous solution than the marketed CMS. In yet another aspect, the present invention provides mixtures of sulfomethylated polymyxins which are more uniform than the marketed CMS. Finally, the present compounds, or the mixtures or compositions thereof, provides for an improved polymyxin dosing and therapy compared with the prior art polymyxin compositions, which is currently not well-defined.

Thus, the present invention provides a novel polymyxin represented by formula (I):

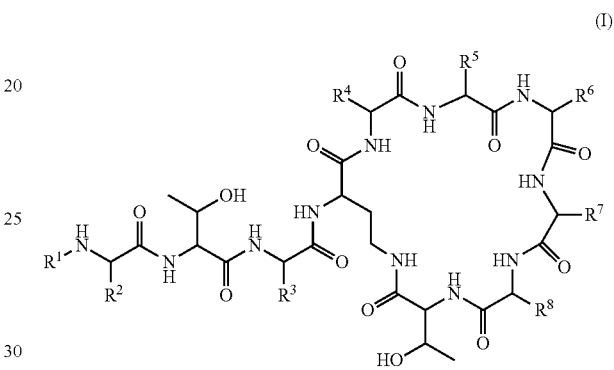

(I)

wherein
$R^1$ is an aliphatic linear or branched $C_6$-$C_{10}$ acyl group, or

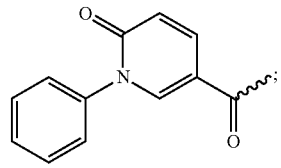

$R^5$ is —$CH(CH_3)_2$, —$CH_2CH(CH_3)_2$, —$CH(CH_3)CH_2CH_3$, or —$CH_2C_6H_5$;
$R^6$ is —$CH(CH_3)_2$, —$CH_2CH(CH_3)_2$, or —$CH(CH_3)CH_2CH_3$;
each of $R^2$, $R^3$, $R^4$, $R^7$ and $R^8$ is either —$(CH_2)_xCH_2NH_2$ or —$(CH_2)_xCH_2N(CH_2SO_3M)_2$;
wherein x is 0 or 1;
wherein M is a cation; and
provided that one of $R^2$, $R^3$, $R^4$, $R^7$ and $R^8$ are —$(CH_2)_xCH_2N(CH_2SO_3M)_2$.

According to one embodiment of the present invention, polymyxins are provided, represented by the formula (I); wherein two sulfomethyl groups are attached to the same γ-amino group.

According to yet another embodiment of the present invention, polymyxins represented by formula (I) are provided, wherein $R^1$ is an aliphatic linear or branched $C_6$-$C_{10}$ acyl group;
$R^5$ and $R^6$ is —$CH_2CH(CH_3)_2$;
each of $R^3$, $R^4$, $R^7$ and $R^8$ is —$CH_2CH_2NH_2$;
and;
$R^2$ is —$CH_2CH_2N(CH_2SO_3M)_2$.
wherein M is a monovalent cation.

According to yet another embodiment of the present invention, polymyxins represented by formula (I) are provided, wherein $R^1$ is an aliphatic linear or branched $C_6$-$C_{10}$ acyl group;
$R^5$ and $R^6$ is —$CH_2CH(CH_3)_2$;
each of $R^2$, $R^4$, $R^7$ and $R^8$ is —$CH_2CH_2NH_2$;
and;
$R^3$ is —$CH_2CH_2N(CH_2SO_3M)_2$.
wherein M is a monovalent cation.

According to yet another embodiment of the present invention, polymyxins represented by formula (I) are provided, wherein $R^1$ is an aliphatic linear or branched $C_6$-$C_{10}$ acyl group;
$R^5$ and $R^6$ is —$CH_2CH(CH_3)_2$;
each of $R^2$, $R^3$, $R^7$ and $R^8$ is —$CH_2CH_2NH_2$;
and;
$R^4$ is —$CH_2CH_2N(CH_2SO_3M)_2$.
wherein M is a monovalent cation.

According to yet another embodiment of the present invention, polymyxins represented by formula (I) are provided, wherein $R^1$ is an aliphatic linear or branched $C_6$-$C_{10}$ acyl group;
$R^5$ and $R^6$ is —$CH_2CH(CH_3)_2$;
each of $R^2$, $R^3$, $R^4$, and $R^8$ is —$CH_2CH_2NH_2$;
and;
$R^7$ is —$CH_2CH_2N(CH_2SO_3M)_2$.
wherein M is a monovalent cation.

According to yet another embodiment of the present invention, polymyxins represented by formula (I) are provided, wherein $R^1$ is an aliphatic linear or branched $C_6$-$C_{10}$ acyl group;
$R^5$ and $R^6$ is —$CH_2CH(CH_3)_2$;
each of $R^2$, $R^3$, $R^4$, and $R^7$ is —$CH_2CH_2NH_2$;
and;
$R^8$ is —$CH_2CH_2N(CH_2SO_3M)_2$.
wherein M is a monovalent cation.

According to yet another embodiment of the present invention, polymyxins represented by formula (I) are provided, wherein $R^1$ is an aliphatic linear or branched $C_6$-$C_{10}$ acyl group;
$R^5$ and $R^6$ is either —$CH_2CH(CH_3)_2$ or $CH_2C_6H_5$;
each of $R^3$, $R^4$, $R^7$ and $R^8$ is —$CH_2CH_2NH_2$;
and;
$R^2$ is —$CH_2CH_2N(CH_2SO_3M)_2$.
wherein M is a monovalent cation.

According to yet another embodiment of the present invention, polymyxins represented by formula (I) are provided, wherein $R^1$ is an aliphatic linear or branched $C_6$-$C_{10}$ acyl group;
$R^5$ and $R^6$ is either —$CH_2CH(CH_3)_2$ or $CH_2C_6H_5$;
each of $R^2$, $R^4$, $R^7$ and $R^8$ is —$CH_2CH_2NH_2$;
and;
$R^3$ is —$CH_2CH_2N(CH_2SO_3M)_2$.
wherein M is a monovalent cation.

According to yet another embodiment of the present invention, polymyxins represented by formula (I) are provided, wherein $R^1$ is an aliphatic linear or branched $C_6$-$C_{10}$ acyl group;
$R^5$ and $R^6$ is either —$CH_2CH(CH_3)_2$ or $CH_2C_6H_5$;
each of $R^2$, $R^3$, $R^7$ and $R^8$ is —$CH_2CH_2NH_2$;
and;
$R^4$ is —$CH_2CH_2N(CH_2SO_3M)_2$.
wherein M is a monovalent cation.

According to yet another embodiment of the present invention, polymyxins represented by formula (I) are provided, wherein $R^1$ is an aliphatic linear or branched $C_6$-$C_{10}$ acyl group;
$R^5$ and $R^6$ is either —$CH_2CH(CH_3)_2$ or $CH_2C_6H_5$;
each of $R^2$, $R^3$, $R^4$, and $R^8$ is —$CH_2CH_2NH_2$;
and;
$R^7$ is —$CH_2CH_2N(CH_2SO_3M)_2$.
wherein M is a monovalent cation.

According to yet another embodiment of the present invention, polymyxins represented by formula (I) are provided, wherein $R^1$ is an aliphatic linear or branched $C_6$-$C_{10}$ acyl group;
$R^5$ and $R^6$ is either —$CH_2CH(CH_3)_2$ or $CH_2C_6H_5$;
each of $R^2$, $R^3$, $R^4$, and $R^7$ is —$CH_2CH_2NH_2$;
and;
$R^8$ is —$CH_2CH_2N(CH_2SO_3M)_2$.
wherein M is a monovalent cation.

According to another aspect of the above embodiments of the present invention, $R^1$ is 6-methyloctanoyl.

According to another aspect of the above embodiments of the present invention, $R^1$ is 6-methyl-heptanoyl.

According to yet another embodiment of the present invention, polymyxins of formula (I) are provided wherein $R^1$ is an aliphatic linear or branched $C_6$-$C_{10}$ acyl group, or

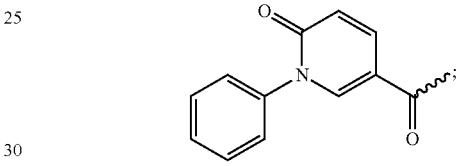

$R^5$ is —$CH(CH_3)_2$, —$CH_2CH(CH_3)_2$, —$CH(CH_3)CH_2CH_3$, or —$CH_2C_6H_5$;
$R^6$ is —$CH(CH_3)_2$, —$CH_2CH(CH_3)_2$, or —$CH(CH_3)CH_2CH_3$;
each of $R^2$, $R^3$, $R^4$, $R^7$ and $R^8$ is either $CH_2NH_2$ or $CH_2N(CH_2SO_3M)_2$;
wherein M is a cation; and
provided that one of $R^2$, $R^3$, $R^4$, $R^7$ and $R^8$ are $CH_2N(CH_2SO_3M)_2$.

The present invention furthermore provides a pharmaceutical composition comprising one or more of the polymyxins according to the present invention.

The composition according to the present invention may furthermore comprise one or more pharmaceutically acceptable excipients.

According to one embodiment, the pharmaceutical composition according to the present invention comprises more than 50% as measured by HPLC of the polymyxins according to the present invention.

According to yet another embodiment, the pharmaceutical composition according to the present invention comprises more than 50% as measured by HPLC of the polymyxins represented by formula (I).

According to yet another embodiment, the pharmaceutical composition according to the present invention comprises more than 80% as measured by HPLC of the polymyxins represented by formula (I).

According to yet another embodiment, the pharmaceutical composition according to the present invention comprises more than 90% as measured by HPLC of the polymyxins represented by formula (I).

According to yet another embodiment, the present composition comprises more than 50% as measured by HPLC of one or more of the polymyxins represented by the formulas of FIGS. 1-5.

According to yet another embodiment, the present composition comprises more than 80% as measured by HPLC of one or more of the polymyxins represented by the formulas of FIG. 1-5.

According to yet another embodiment, the present composition comprises more than 90% as measured by HPLC of one or more of the polymyxins represented by the formulas of FIG. 1-5.

A first embodiment is directed to a polymyxin represented by formula (I):

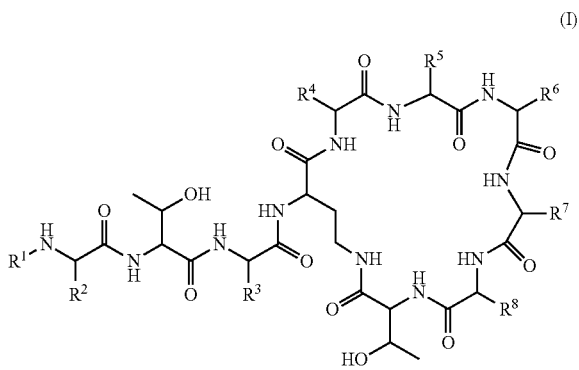

(I)

wherein

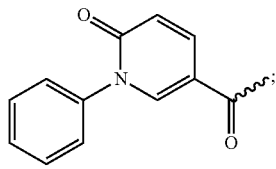

$R^1$ is an aliphatic linear or branched $C_6$-$C_{10}$ acyl group, or
$R^5$ is —CH(CH$_3$)$_2$, —CH$_2$CH(CH$_3$)$_2$, —CH(CH$_3$)CH$_2$CH$_3$, or —CH$_2$C$_6$H$_5$;
$R^6$ is —CH(CH$_3$)$_2$, —CH$_2$CH(CH$_3$)$_2$, —CH(CH$_3$)CH$_2$CH$_3$ or —CH$_2$CH$_2$CH$_3$;
each of $R^2$, $R^3$, $R^4$, $R^7$ and $R^8$ is either —(CH$_2$)$_x$CH$_2$NH$_2$ or —(CH$_2$)$_x$CH$_2$N(CH$_2$SO$_3$M)$_2$;
wherein x is 0 or 1;
wherein M is a cation; and
wherein one of $R^2$, $R^3$, $R^4$, $R^7$ and $R^8$ is —(CH$_2$)$_x$CH$_2$N(CH$_2$SO$_3$M)$_2$.

In a first aspect of the first embodiment, R1 is heptanoyl, methylheptanoyl, octanoyl, methyloctanoyl, nonanoyl, methylnonanoyl or decanoyl.

In a second aspect of the first embodiment, R1 is heptanoyl, 6-methylheptanoyl, octanoyl, (S)-6-methyloctanoyl, 7-methyloctanoyl, 3-hydroxy-6-methyloctanoyl, nonanoyl, (8-methylnonanoyl or decanoyl.

In a third aspect of the first embodiment, the previously described polymyxins are characterized in that M is selected from the group consisting of Na$^+$, K$^+$, ½Mg$^{2+}$, H$_m$N(C$_{1-4}$alkyl)$_n^+$, or combinations thereof, where m is 0-4 and n is 0-4 with the proviso that m+n=4.

In a fourth aspect of the first embodiment, x is 1 and M is H$^+$, Na$^+$ or K$^+$.

In a fifth aspect of the first embodiment, x is 1 and M is Na$^+$ or K$^+$.

A second embodiment is directed to a composition comprising at least one polymyxin represented by formula (I):

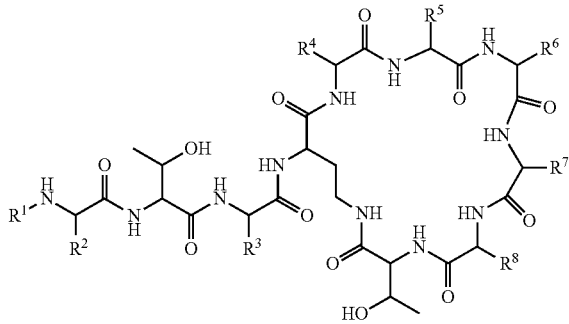

(I)

wherein

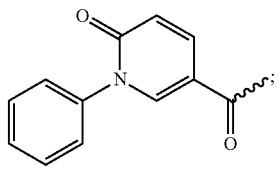

$R^1$ is an aliphatic linear or branched $C_6$-$C_{10}$ acyl group, or
$R^5$ is —CH(CH$_3$)$_2$, —CH$_2$CH(CH$_3$)$_2$, —CH(CH$_3$)CH$_2$CH$_3$, or —CH$_2$C$_6$H$_5$;
$R^6$ is —CH(CH$_3$)$_2$, —CH$_2$CH(CH$_3$)$_2$, —CH(CH$_3$)CH$_2$CH$_3$ or —CH$_2$CH$_2$CH$_3$;
each of $R^2$, $R^3$, $R^4$, $R^7$ and $R^8$ is either —(CH$_2$)$_x$CH$_2$NH$_2$ or —(CH$_2$)$_x$CH$_2$N(CH$_2$SO$_3$M)$_2$;
wherein x is 0 or 1;
wherein M is a cation; and
wherein one of $R^2$, $R^3$, $R^4$, $R^7$ and $R^8$ is —(CH$_2$)$_x$CH$_2$N(CH$_2$SO$_3$M)$_2$.

In a first aspect of the second embodiment, R1 is heptanoyl, methylheptanoyl, octanoyl, methyloctanoyl, 3-hydroxy-6-methyloctanoyl, nonanoyl, methylnonanoyl or decanoyl.

In a second aspect of the second embodiment, R1 is heptanoyl, 6-methylheptanoyl, octanoyl, (S)-6-methyloctanoyl, 3-hydroxy-6-methyloctanoyl, 7-methyloctanoyl, nonanoyl, 8-methylnonanoyl or decanoyl.

In a third aspect of the second embodiment, the previously described polymyxins are characterized in that M is selected from the group consisting of Na$^+$, K$^+$, H$_m$N(C$_{1-4}$alkyl)$_n^+$, ½Mg$^{2+}$ or combinations thereof, where m is 0-4 and n is 0-4 with the proviso that m+n=4.

In a fourth aspect of the second embodiment, x is 1 and M is H$^+$, Na$^+$ or K$^+$.

In a fifth aspect of the second embodiment, x is 1 and M is Na$^+$ or K$^+$.

In a sixth aspect of the second embodiment, the pharmaceutical composition comprises more than 50% as measured by HPLC of the polymyxins represented by formula (I).

In a seventh aspect of the second embodiment, the pharmaceutical composition comprises more than 50% as measured by HPLC of the polymyxins represented by formula (I) and x is 1 and M is Na$^+$ or K$^+$.

A third embodiment is directed to a polymyxin represented by formula (I):

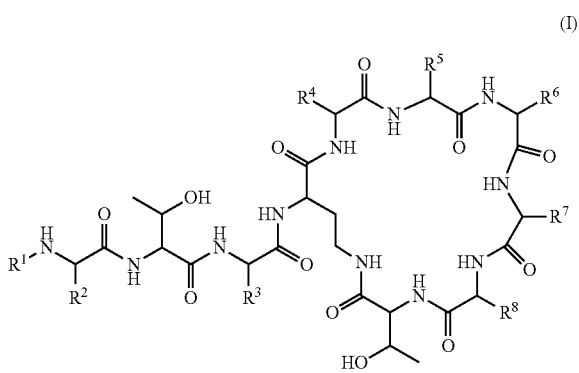

wherein
R¹ is an aliphatic linear or branched $C_6$-$C_{10}$ acyl group;
R⁵ is —$CH_2CH(CH_3)_2$ or —$CH_2C_6H_5$;
R⁶ is —$CH_2CH(CH_3)_2$;
each of R², R³, R⁴, R⁷ and R⁸ is either —$CH_2CH_2NH_2$ or —$CH_2CH_2N(CH_2SO_3M)_2$;
wherein M is a cation; and
wherein only one of R², R³, R⁴, R⁷ and R⁸ is —$CH_2CH_2N(CH_2SO_3M)_2$.

In a first aspect of the third embodiment, the aliphatic $C_6$-$C_{10}$ acyl group or the branched $C_6$-$C_{10}$ acyl group optionally contains a hydroxyl group.

A fourth embodiment is directed to a composition comprising at least one polymyxin represented by formula (I):

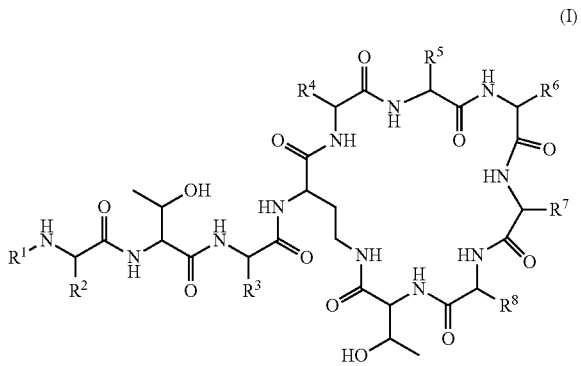

wherein
R¹ is an aliphatic linear or branched $C_6$-$C_{10}$ acyl group;
R⁵ is —$CH_2CH(CH_3)_2$, or —$CH_2C_6H_5$;
R⁶ is —$CH_2CH(CH_3)_2$;
each of R², R³, R⁴, R⁷ and R⁸ is either —$CH_2CH_2NH_2$ or —$CH_2CH_2N(CH_2SO_3M)_2$;
wherein M is a cation; and
wherein only one of R², R³, R⁴, R⁷ and R⁸ is —$CH_2CH_2N(CH_2SO_3M)_2$.

In a first aspect of the fourth embodiment, the pharmaceutical composition comprises more than 50% as measured by HPLC of the polymyxins represented by formula (I).

In a second aspect of the fourth embodiment, the pharmaceutical composition comprises more than 80% as measured by HPLC of the polymyxins represented by formula (I).

In a third aspect of the fourth embodiment, the pharmaceutical composition comprises more than 50% as measured by HPLC of the polymyxins represented by formula (I) and is used for treatment of infections caused by Gram-negative bacteria.

In a fourth aspect of the fourth embodiment, the pharmaceutical composition comprises more than 50% as measured by HPLC of the polymyxins represented by formula (I) and M is selected from pharmaceutically acceptable cations.

In a fifth aspect of the fourth embodiment, the pharmaceutical composition comprises more than 50% as measured by HPLC of the polymyxins represented by formula (I) and M is selected from pharmaceutically acceptable monovalent cations.

In a sixth aspect of the fourth embodiment, the aliphatic $C_6$-$C_{10}$ acyl group or the branched $C_6$-$C_{10}$ acyl group optionally contains a hydroxyl group.

A fifth embodiment is directed to a composition comprising at least one polymyxin represented by formula (I):

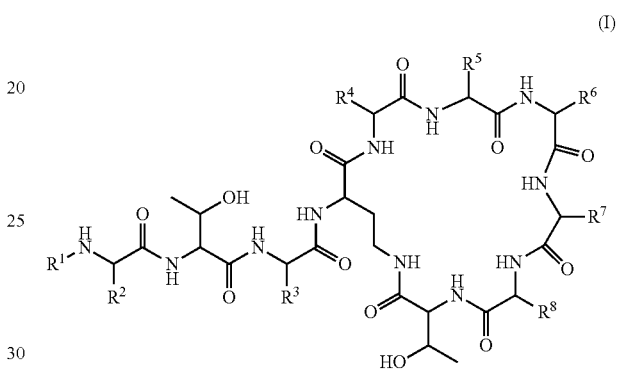

wherein
R¹ is 6-methyloctanoyl, 6-methylheptanoyl or octanoyl;
R⁵ is —$CH_2CH(CH_3)_2$, or —$CH_2C_6H_5$;
R⁶ is —$CH_2CH(CH_3)_2$;
each of R², R³, R⁴, R⁷ and R⁸ is either —$CH_2CH_2NH_2$ or —$CH_2CH_2N(CH_2SO_3Na)_2$; and
wherein only one of R², R³, R⁴, R⁷ and R⁸ is —$CH_2CH_2N(CH_2SO_3Na)_2$.

In a first aspect of the fifth embodiment, the pharmaceutical composition comprises more than 50% as measured by HPLC of the polymyxins represented by formula (I).

In a second aspect of the fifth embodiment, the pharmaceutical composition comprises more than 80% as measured by HPLC of the polymyxins represented by formula (I).

In a third aspect of the fifth embodiment, the pharmaceutical composition comprises more than 50% as measured by HPLC of the polymyxins represented by formula (I) and is used for treatment of infections caused by Gram-negative bacteria.

DETAILED DESCRIPTION

Brief Description of the Figures

FIG. 13 (bottom) shows the extracted ion current (EIC) for masses corresponding to mono(bis-sulfomethylated) Polymyxin E1 (m/z of 677.62, 1356.2, 1378.06).

DEFINITIONS

Figure 1:
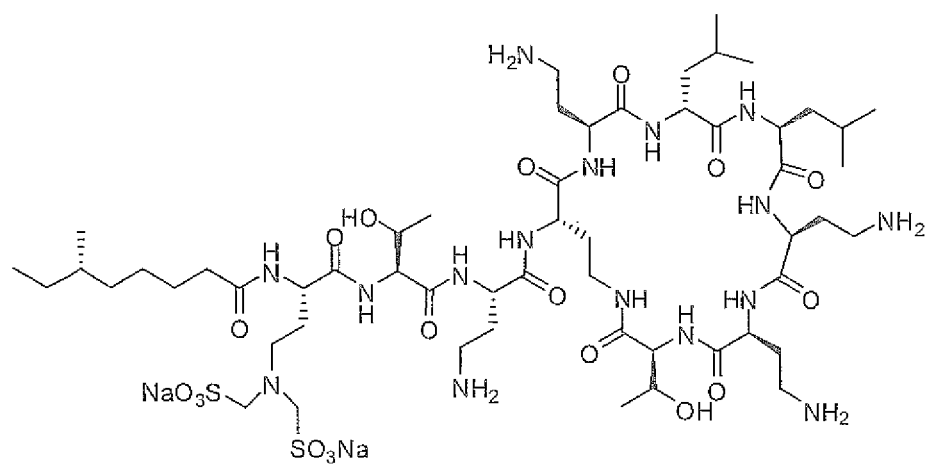
FIG. 1 shows the structure of the disodium salt of PE1-$(SM)_2^1$
Figure 2:
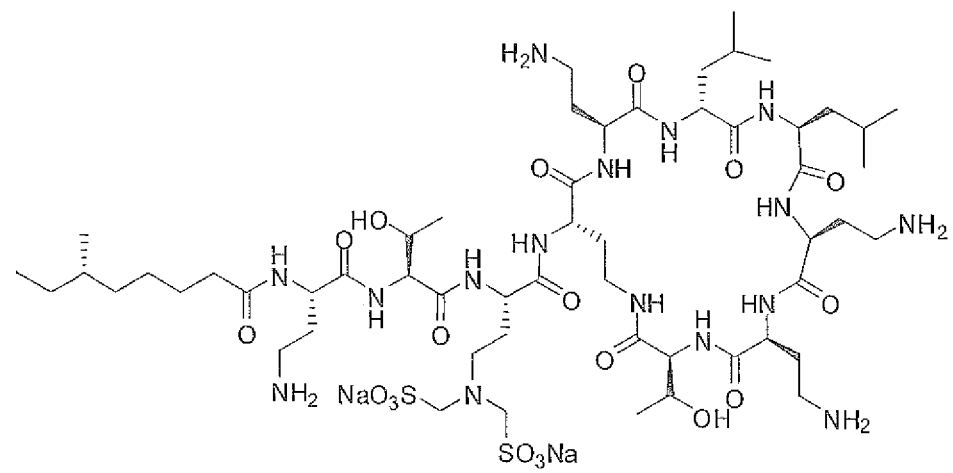
FIG. 2 shows the structure of disodium salt of PE1-$(SM)_2^3$
Figure 3:
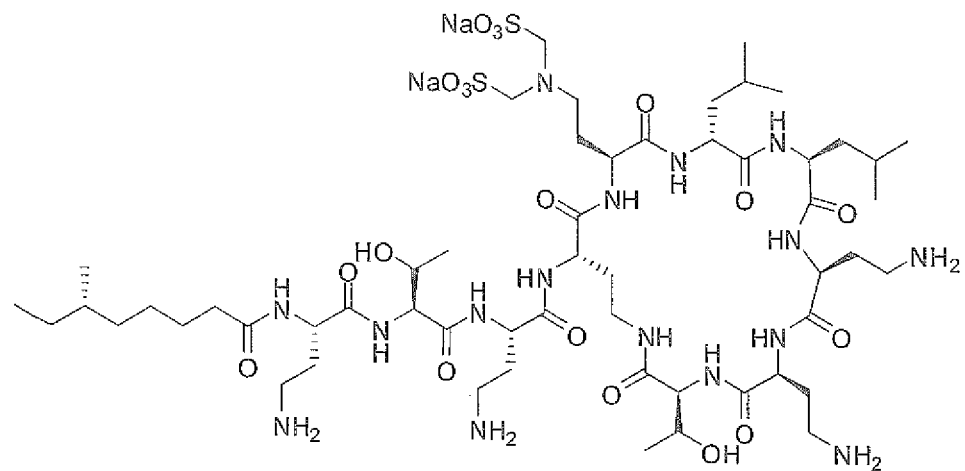
FIG. 3 shows the structure of disodium salt of PE1-$(SM)_2^5$
Figure 4:
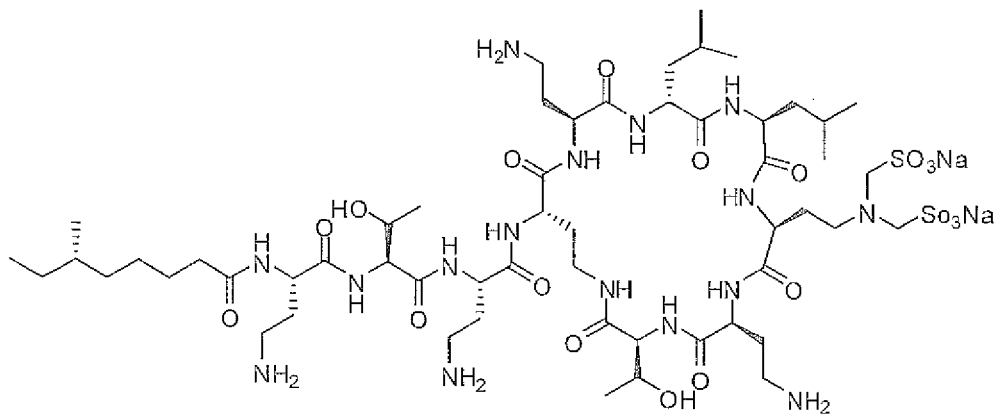
FIG. 4 shows the structure of disodium salt of PE1-$(SM)_2^8$

As used throughout this specification and the appended claims, the following terms have the following meanings:

The term "polymyxin" as described herein refers to antibiotic compounds comprising a peptide moiety amide-coupled to a fatty acid moiety.

The term "Dab residue" as described herein, refers to a 2,4-diaminobutyrate compound amide-coupled to at least one amino acid. The naturally occurring polymyxins usually comprise 6 Dab residues of which 5 have a free γ-amino group.

The term "Dab" as described herein, refers the radical derived from 2,4-diaminobutanoic acid, in which the carbon atom adjacent to the carbonyl carbon (i.e., the α-carbon) has a stereochemistry designated as the L-configuration. L-Dab is alternatively referred to in the literature as L-Dbu.

The amino acid in position 6 in the polymyxins represented by formula (I) have D-configuration, i.e. the amino acid residue to which $R^5$ is attached.

The term "DAP residue" as described herein refers to a 2,3-diaminopropionate compound amide-coupled to at least one amino acid.

The term "DAP" as described herein refers to the compound 2,3-diaminopropionate.

The term "sulfomethyl" as described herein refers to the —CH$_2$SO$_3$M moiety, where M is as defined below. The sulfonate (—SO$_3$) moiety can be in acidic form, but in a physiologic environment (in vivo) it will have a negative charge and will have an associated cation, such as M.

The term "CMS" as described herein refers to a composition comprising sulfomethylated Colistin. Chemical abstracts have assigned such a composition the number 8068-28-8 for CMS.

The term "CMS E1" as described herein refers to a composition made from sulfomethylation of relatively pure Polymyxin E1 (>80% pure by HPLC).

The term "Colistin" as described herein refers to a composition comprising polymyxin E1 and polymyxin E2. Chemical abstracts have assigned the number 1066-17-7 for Colistin. According to the European pharmacopoeia, Colistin should comprise more than 77% of Polymyxin E1, E2, E3, E1i and E1-7MOA, but less than 10% of each of the minor components Polymyxin E3, E1-i and E1-7MOA.

The term "Polymyxin E" as described herein is used interchangeably with "Colistin".

The term "Polymyxin E1" as described herein refers to the compound having the CAS no 7722-44-3. Polymyxin E1 is used interchangeably with Colistin A.

The term "Polymyxin E2" as described herein refers to the compound having the CAS no 7239-48-7. Polymyxin E2 is used interchangeably with Colistin B.

The expression "sulfomethylated polymyxin" as described herein refers to a polymyxin comprising at least one sulfomethyl group attached to a γ-amino group on a L-DAB residue.

The term "M" is a cation and refers to a cationic species containing one or two positive charges, examples of which include, but are not limited to Li$^+$, Na$^+$, K$^+$, ½Mg$^{2+}$, H$_m$N(C$_{1-4}$alkyl)$_n$$^+$, where m is 0-4 and n is 0-4 with the proviso that m+n=4.

The expression "an aliphatic linear or branched C6-C10 acyl group," as described herein, refers to a substituent containing a carbonyl moiety and a non-carbonyl moiety containing a total of 6 to 10 carbon atoms. It includes the acyl groups found in known polymyxin compounds. It also includes, but is not limited to, heptanoyl, methylheptanoyl (including (S)-6-methylheptanoyl), octanoyl, methyloctanoyl (including (S)-6-methyloctanoyl, 7-methyloctanoyl), nonanoyl, methylnonanoyl and decanoyl.

The term "salts" or "salt thereof as described herein, refers to a compound comprising a cation and an anion, which can prepared by any process known to one of ordinary skill, e.g., by the protonation of a proton-accepting moiety and/or deprotonation of a proton-donating moiety. Alternatively, the salt can be prepared by either a cation/anion metathesis or a cation/anion exchange reaction.

The term "more than X % as measured by HPLC" as described herein is to be understood as the relative integrated area of the pertaining peak(s) in the chromatogram resulting from an HPLC method as described in the examples of this application or alternatively as described in WO2014195405A1.

According to the present invention, novel polymyxins are provided comprising two sulfomethyl groups which are attached to any of the Dab residues of the above structure having a free γ-amine, i.e. any of the Dab residues Dab 1, Dab3, Dab5, Dab8 or Dab9. Thus, formula (I) is meant to cover mono(bis-sulfomethylated) polymyxins, but not the tri-, tetra- or penta(bis-sulfomethylated) polymyxins.

Figure 5:
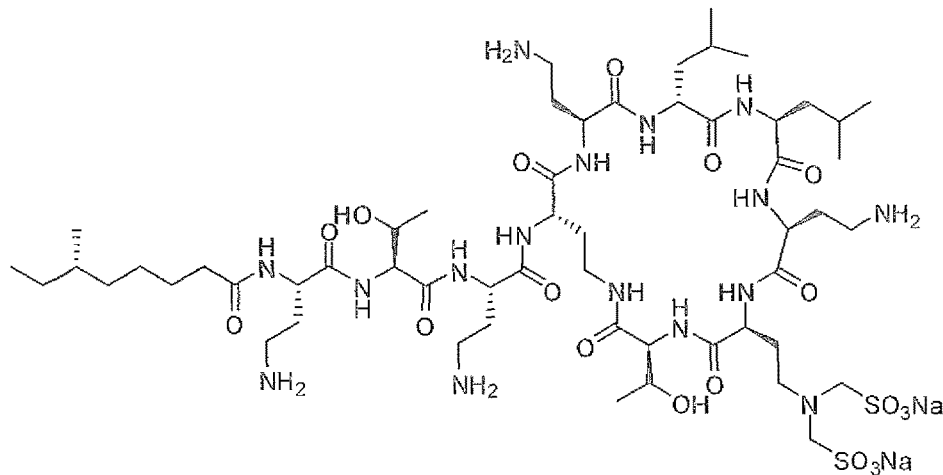
FIG. 5 shows the structure of disodium salt of PE1-$(SM)_2^9$
Figure 6:
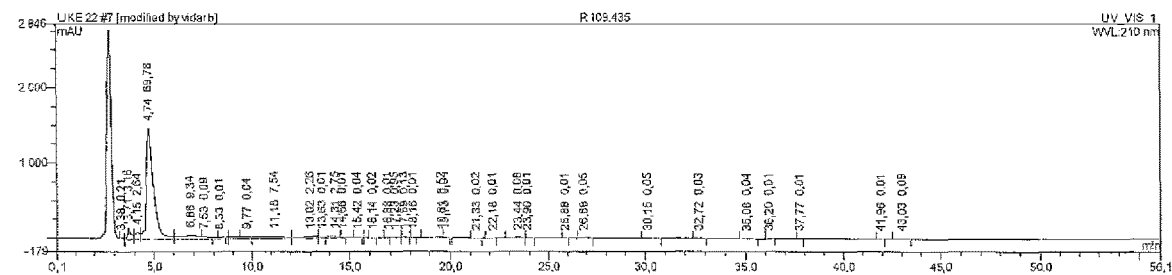
FIG. 6 shows a chromatogram of PE1-$(SM)_{10}^{1,3,5,8,9}$
Figure 7:
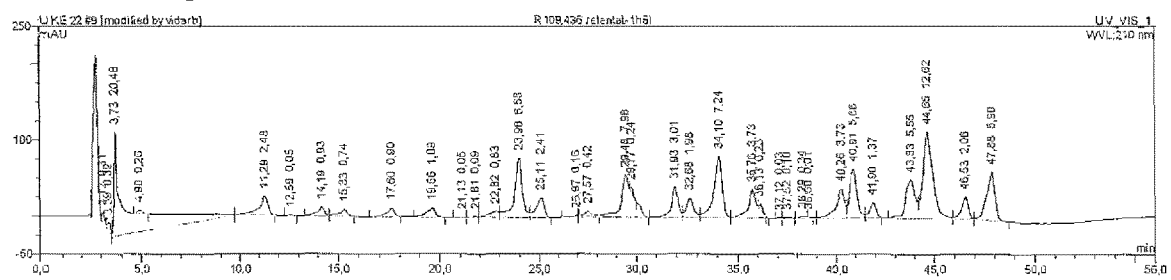
FIG. 7 shows the degradation of PE1-(SM)$_{10}$$^{1,3,5,8,9}$ under non-equilibrium conditions after 90 min, pH 9.
Figure 8:
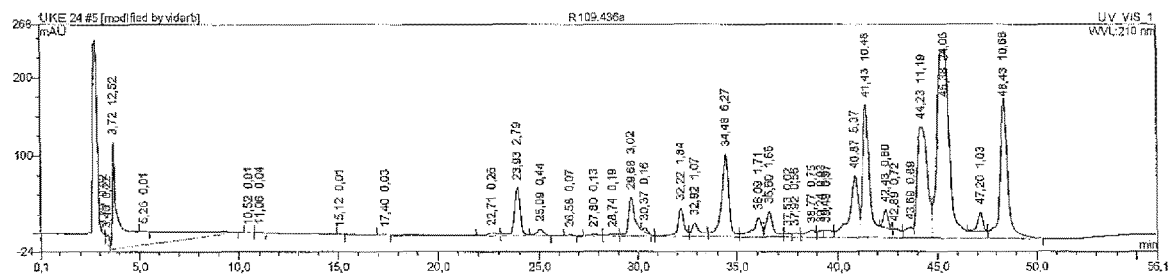
FIG. 8 shows the degradation of PE1-(SM)$_{10}$$^{1,3,5,8,9}$ under non-equilibrium conditions after 3 days, pH 8.0.
Figure 9:
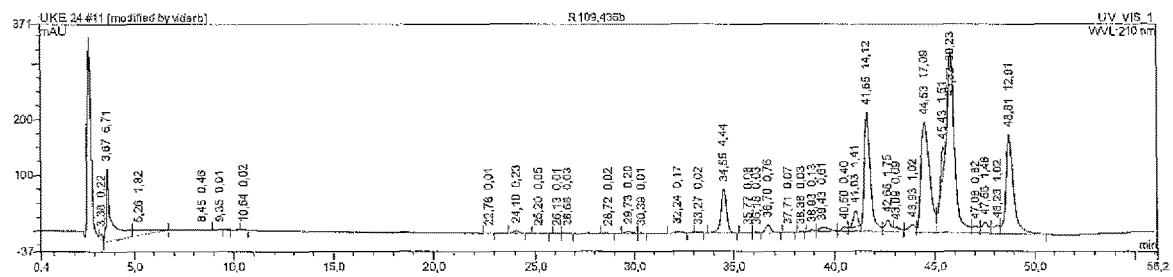
FIG. 9 shows the degradation of PE1-(SM)$_{10}$$^{1,3,5,8,9}$ under non-equilibrium conditions after 3 days, pH 7.0.
Figure 10:
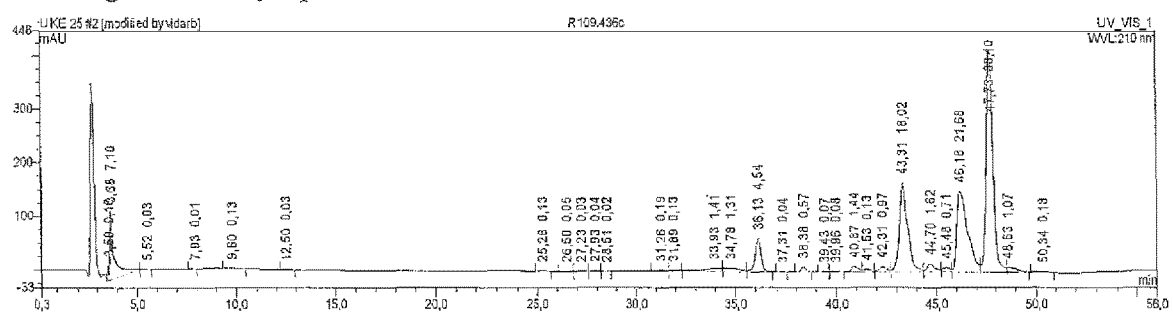
FIG. 10 shows the degradation of PE1-(SM)$_{10}$$^{1,3,5,8,9}$ under non-equilibrium conditions after 3 days, pH 6.5.
Figure 11:
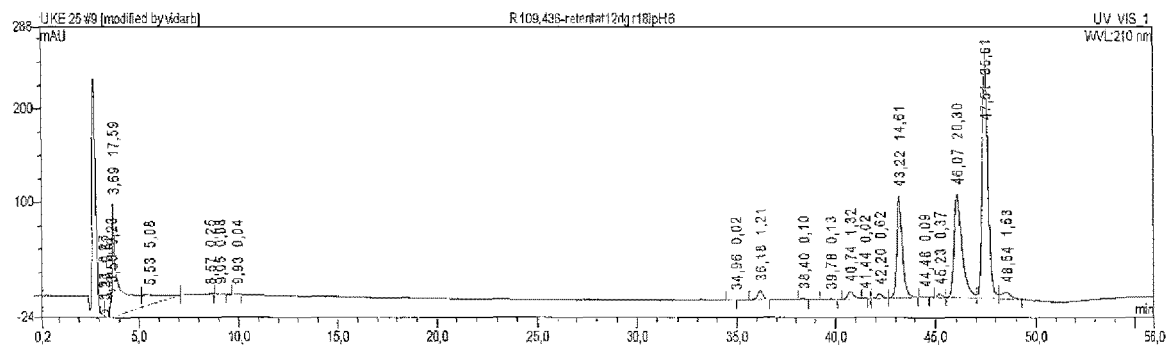
FIG. 11 shows the degradation of PE1-(SM)$_{10}$$^{1,3,5,8,9}$ under non-equilibrium conditions after 3 days, pH 6.0.

An example of the new polymyxins is designated herein as mono (N$^γ$-bis-sulfomethyl) Dab$^9$ polymyxin E1, i.e. wherein the substituents of formula I is represented by $R^1$ being 6-methyloctanoyl, $R^5$ and $R^6$ is —CH$_2$CH(CH$_3$)$_2$; each of $R^2$, $R^3$, $R^4$, and $R^7$ is —CH$_2$CH$_2$NH$_2$; and $R^8$ is —CH$_2$CH$_2$N(CH$_2$SO$_3$M)$_2$ wherein M is Na$^+$. An example of such a compound is shown in FIG. 5. The abbreviated name for this compound is PE1-(SM)$_2$$^9$.

Other examples of mono bis-sulfomethylated polymyxins are mono (N$^γ$-bis-sulfomethyl) Dab$^1$ polymyxin E1, mono (N$^γ$-bis-sulfomethyl) Dab$^3$ polymyxin E1, mono (N$^γ$-bis-sulfomethyl) Dab$^5$ polymyxin E1, mono (N$^γ$-bis-sulfomethyl) Dab$^8$ polymyxin E1, of which the disodium structures are shown in FIG. 1-4, respectively.

The expression "—CH$_2$CH$_2$NH$_2$" is understood to cover either —CH$_2$CH$_2$NH$_2$ or —CH$_2$CH$_2$NH$_3$$^+$ depending on the pH of the medium.

The expression "—CH$_2$NH$_2$" is understood to cover either —CH$_2$NH$_2$ or —CH$_2$NH$_3$$^+$ depending on the pH of the medium.

The polymyxins as described herein embrace many molecular species. For example in aqueous solutions, the charge will depend on pH. The polymyxin compounds as described herein cover all pharmaceutical acceptable salts and ions thereof. Among such polymyxins are of course the di-sodium salts. Other pharmaceutically acceptable salts are also included e.g. potassium, lithium, and ammonium salts (such as $H_mN(C_{1-4}alkyl)_n^+$ where m is 0-4 and n is 0-4 with the proviso that m+n=4), or combinations thereof.

The polymyxins as described herein may be used in the treatment or prevention of infectious disorders, in particularly infections caused by Gram-negative bacteria, such as, but not limited to, *Pseudomonas aeruginosa, Klemsiella pneumonia*, and *Acinetobacter baumannii, Eschericia coli*, and *Enterobacter aerogenes*. According to one aspect, the present invention includes the use of a pharmaceutical composition comprising an effective amount of any of the compositions described herein in the treatment of a gram negative bacterial infection.

The present compounds may be administered in a therapeutically effective amount. "A therapeutically effective amount" is meant to describe a sufficient quantity of the compound to treat the infection. The skilled person, will acknowledge that the appropriate daily dosage of a particular patients may vary depending upon factors such as the disorder being treated, and the severity thereof; the composition employed, the age, body weight, sex and diet of the patient, and the preferences and experience of the medical practitioner involved, etc.

The compositions according to the present invention may be administered for use in human as well as veterinary medicine. The composition described herein may be administered to a patient in need thereof via various routes, such as subdermal, by inhalation, oral, parenteral or topical route. The composition may be in any form well known to the skilled person, and includes e.g. tablets, capsules, powders, granules, lozenges, creams or liquid preparation, such as sterile paerenteral solutions or suspensions.

In one aspect, the composition is useful for administration by intravenous infusion or injections. An intravenous or injection formulation may be prepared according to methods well known to the skilled person. For example, the compounds described herein can be dissolved in water for injection, followed by filter sterilization, and further followed by transferring said filtered composition to a suitable vial.

According to one aspect, the composition is lyophilized. The lyophilized powder is reconstituted, e.g. in water for injection, prior to use, e.g. prior to administration by injection, or prior to administration by inhalation (e.g. using a nebulizer or any other suitable inhalations devices). Thus, according to another aspect, the composition is formulated for administration is by inhalation.

The compounds described herein may further comprise one or more pharmaceutically acceptable excipients, including but not limited to a preservative, a buffer, and antioxidant, or a diluent. Suitable diluents includes e.g. water for injection, 0.9% NaCl, 5% dextrose in 0.9% NaCl, 5% dextrose in water, 5% dextrose in 0.45% NaCl, 5% dextrose in 0.225% NaCl, and Lactated Ringer's solution.

The compounds disclosed herein may furthermore be administered in combination with one or more additional anti-bacterial agents. The compounds described herein may when used in combination with another anti-bacterial agent be administered simultaneously, separately or sequentially with the one or more other anti-bacterial agent.

The present invention is further illustrated below by way of examples. It is to be understood that the scope of the present invention is in any way limited by the scope of the following examples.

EXAMPLES

The present disclosure is further supported and exemplified by the following experimental section, but is not to be limited thereto.

Example 1

Starting Material

Isolated polymyxin E1 sulfate (3.5 g) and a 45% w/w aqueous solution of sodium hydroxymethanesulfonate (11.3 g) were mixed and warmed to 60° C. while stirring. pH was then kept at 7.0-7.5 by several additions of 2 M NaOH. After 18 hr the mixture was cooled to ambient temperature and the crude product furnished as a white solid by precipitation in 200 mL of methanol/acetonitrile 1/1 v/v.

The product was de-salted and polished by the following procedure: A C18 column 6μ e.g. Phenomenex X Bridge Prep Shield 10×250 mm or similar was washed and equilibrated with 5% MeCN (no salt). The column was mounted in a Waters Delta Prep HPLC system, 150 mL/min maximum flow. The detector was 5 a Waters 2487 adjusted to 280 nm. A mixture of 9 mL 5% MeCN solution of 230 mg PE1-$(SM)_{10}^{1,3,5,8,9}$ and 1 mL 2M NaCl was loaded the column and the flow was 6-8 mL/min.

The column was eluted and desalted with 5% MeCN with 6-8 mL/min and the PE1-$(SM)_{10}^{1,3,5,8,9}$ fraction collected. Some degradation occurred on-column during the process, but by cutting the head and tail off, the high purity is maintained. The Head Fraction, ca. 35 mL, was collected directly into 450 mL 100% MeCN and further 550 mL 100% MeCN was added before vacuum-evaporation of the 97:3 MeCN:$H_2O$ solution in a 2 L pear shaped evaporation flask.

The distillation process was performed with a Büchi 15 Rotavapor. The 94:6 azeotrope distils off making a water free PE1-$(SM)_{10}^{1,3,5,8,9}$-residue in the 2 L vacuum-distillation flask. The residue was removed with 3×8 mL 100% MeOH (dry) and poured into a 50 mL vacuum evaporation flask and vacuum-evaporated to a 1-2 mL MeOH-PE1-$(SM)_{10}^{1,3,5,8,9}$ suspension. 15 mL 100% MeCN was added and the 20 solution/suspension was vacuum-evaporated further to dryness with water bath temperature of 35° C. The pressure was decreased from 70-60 Torr down to 20-15 Torr during the process. Further vacuum-drying was done for 30 min with slow rotation in the 35° C. water bath with maintained vacuum. The yield was 150 mg substance of the PE1-$(SM)_{10}^{1,3,5,8,9}$.

Example 2

Production of a Mixture Comprising Mono ($N^\gamma$-bis-sulfomethyl) Polymyxin E1.

When sulfomethylated polymyxins degrade towards Colistin, hydroxymethane-sulfonate is liberated. The process is reversible as the hydroxymethanesulfonate easily regenerates the parent sulfomethylated molecule.

The purpose of this study was to investigate degradation of sulfomethylated polymyxins under non-equilibrium conditions by the continuous removal of hydroxymethanesulfonate using nanofiltration.

The experiment was set up with 2 L 10 mM PE1-$(SM)_{10}^{1,3,5,8,9}$ in RO water and the volume of the solution was kept constant in the filtration unit by the frequent addition of RO water. The nanofiltration unit was run in daily campaigns at 40 C under 3 bar pressure, removing approx. 5 l of effluent each time. pH was adjusted with 0.1 M HCl until stabile to 8.0, 7.0, 6.5 and 6.0. The results are shown in FIG. 6-11.

Figure 12:
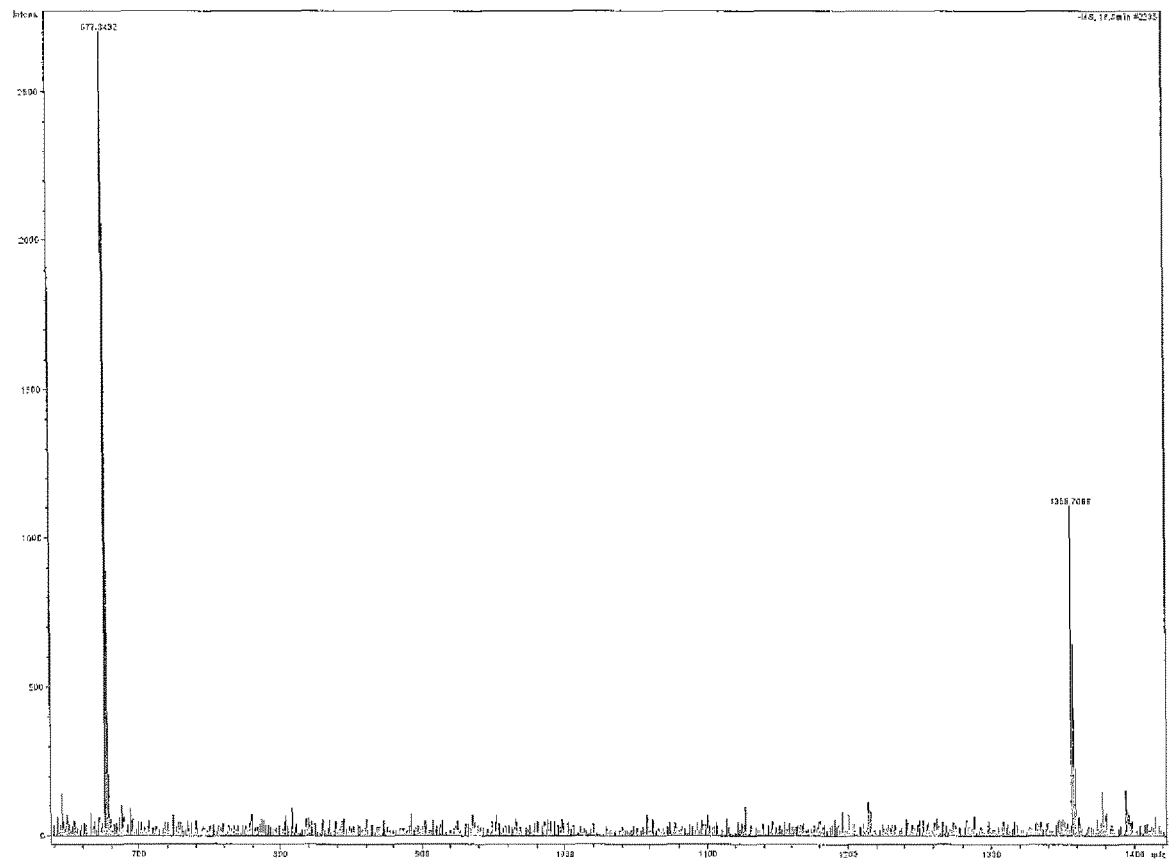
FIG. 12 shows MS spectra obtained for two substituted Polymyxin E1. m/z 677.3 [−2] and 1355.5 [−1] was obtained in negative mode.

MS data confirms di-sulfomethylation of the polymyxins. The FIG. 12 shows the MS spectra obtained, m/z 677.3 [−2] and 1355.5 [−1], in negative mode.

Example 3: Synthesis of Low Substituted Colistins

Colistin sulfate (1.0 g, 0.71 mmol) was dissolved in 20 ml water. 45% sodium hydroxymethanesulfonate (0.847 g, 2.841 mmol) and NaHCO$_3$ (0.12 g, 1.40 mmol) was added. The clear solution was stirred for 12 h at 25° C. The product was precipitated by slow addition of 100 ml acetonitrile and methanol (50:50). The product was isolated as a white powder.

Example 4a: Synthesis of Low Substituted Polymyxin E1

Polymyxin E1 (1.0 g, 0.71 mmol) was dissolved in 20 ml water. 45% sodium hydroxymethanesulfonate (0.847 g, 2.841 mmol) and NaHCO$_3$ (0.12 g, 1.40 mmol) was added. The clear solution was stirred for 12 h at 25° C. The product was precipitated by slow addition of 100 ml acetonitrile and methanol (50:50). The product was isolated as a white powder.

Example 4b: Chromatography and MS of Low Substituted Polymyxin E1

Figure 13:
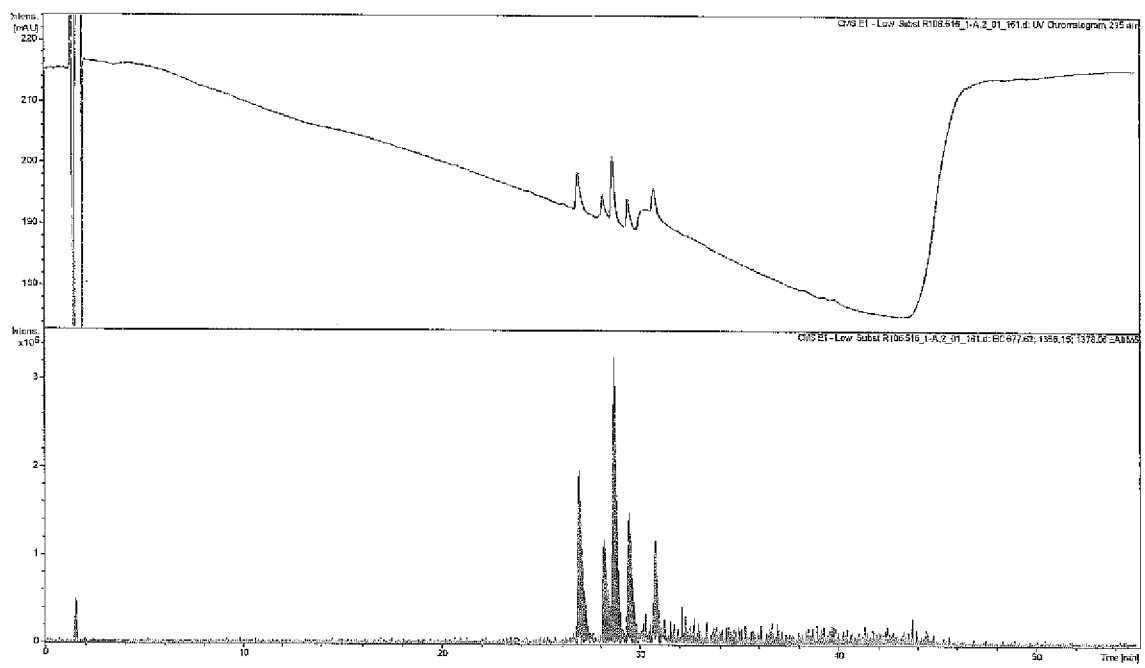
FIG. 13 (top) shows a chromatogram confirming the presence of five individual Polymyxin components comprising two sulfomethyl groups (UV signal at 215 nm).

Mono(bis-sulfomethylated) Polymyxin E1 as made by example 4a was analysed using a Mass Spectrometric (MS in negative mode) and UV compatible method where separation was performed at pH 6.6. The top of FIG. 13 shows a chromatogram confirming the presence of five individual Polymyxin components comprising two sulfomethyl groups (UV signal at 215 nm). The bottom of FIG. 13 shows the extracted ion current (EIC) for masses corresponding to mono(bis-sulfomethylated) Polymyxin E1 (m/z of 677.62, 1356.2, 1378.06).

Figure 14:
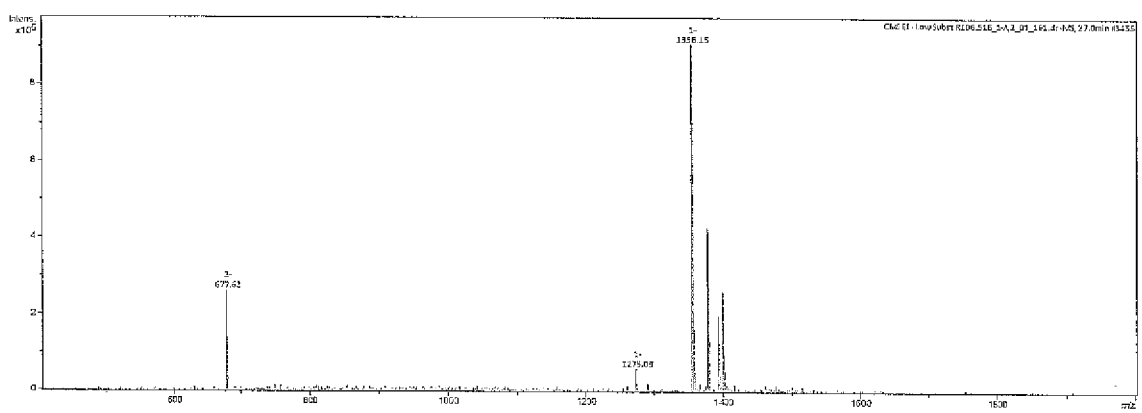
FIG. 14 shows mass spectra of mono(bis-sulfomethylated) polymyxin E1.

FIG. 14 shows the individual mass spectra of mono(bis-sulfomethylated) polymyxin E1. The m/z of 677 corresponds to [M+2H]2+, 1356 corresponds to [M+H]+, and 1378 corresponds to [M+Na]+ of mono(bis-sulfomethylated) Polymyxin E1.

Example 5: MIC

A sample comprising ca. 93% mono(N$^\gamma$-bis-sulfomethyl) Polymyxin E1 was subjected to MIC analysis against *Bordetella bronchiseptica*, ATCC 4617 and the microbial potency was measured to be 611 µg/g.

MIC Assay

Test organisms were cultured in shakeflasks for approx. 16 hours at 250 rpm, 34° C. for *Pseudomonas aeruginosa* and 37° C. for *Klebsiella baumannii* and *Acinetobacter baumannii*. They were re-cultured to late log, diluted to concentrations ready to use and frozen with glycerol at ÷75° C. The medium used was Mueller Hinton Broth.

Samples were prepared by dissolving 5 mg of the compounds in 1 ml Mueller Hinton Broth. The samples were diluted and added to the wells, test organisms were added and after approx. 16 hours incubation at 37° C. with shaking for *Klebsiella baumannii* and *Acinetobacter baumannii*, at 34° C. without shaking for *Pseudomonas aeruginosa*, the growth inhibition was measured by OD$_{600}$. Results are provided in Table 1.

TABLE 1

| Sample | P. aeruginosa | K. pneumoniae | A. baumannii |
|---|---|---|---|
| mono (N$^\gamma$-bis-sulfomethyl) Polymyxin E1 | 4 µg/ml | 8 µg/ml | 4 µg/ml |
| Colistin | 2 µg/ml | 4 µg/ml | 0.5 µg/ml |
| CMS | 4 µg/ml | 8 µg/ml | 4 µg/ml |

Example 6: Toxicity of the Compounds of the Present Invention

Nephrotoxicity was measured using KIM-1 (kidney injury molecule-1) as a biomarker of acute tubular necrosis.

Mice were treated with a mixture comprising 93% mono (N$^\gamma$-bis-sulfomethyl) Polymyxin E1 or CMS for 5 days and were monitored for clinical signs of toxicity and urine concentrations of KIM-1. During the 5 days of treatment mice showed no clinical signs of toxicity. KIM-1 levels in urine indicated a slight increase compared to vehicle treatment. The normal range of KIM-1 in mouse urine, as stated in the ELISA kit instruction, is 456-8048 pg/ml.

The mixtures were received as dry powder and were dissolved in the vials in sterile saline to the concentration stated in table 1, immediately prior to injection.

Once a day for 5 days, mice were treated subcutaneously in the neck region with 0.2 ml corresponding to the doses stated in Table 1. The dosing was based on a mean weight of 28 g.

Urine samples were collected at 24 hrs after the 2nd dosing and 4 hrs after the 5th dosing. Samples were stored at −80° C. until analysed for KIM-1 concentrations Urine samples were thawed, centrifuged for 5 min at 2000 g and diluted ×50 prior to performing the ELISA according the instruction in the Quantikine ELISA mouse TIM-1/KIM-1/HAVCR Immunoassay kit.

TABLE 1

| | Treatment schedule | |
|---|---|---|
| Treatment: Dose | Concentration of dosing solution | Number of Mice |
| A mixture comprising 93% mono (N$^\gamma$-bis-sulfomethyl) Polymyxin E1: 25 mg/kg | 3.5 mg/ml | 5 |
| a mixture comprising 93% mono (N$^\gamma$-bis-sulfomethyl) Polymyxin E1: 30 mg/kg | 4.3 mg/ml | 5 |
| CMS: 32 mg/kg | 4.7 mg/ml | 5 |
| Gentamicin: 80 mg/kg | 12 mg/ml | 5 |
| Vehicle | | 5 |

All the tested mixtures were well tolerated by mice as determined by body weight and clinical scoring. Thickened skin at the site of injection was observed in the groups of mice injected with a mixture comprising 93% mono (N$^\gamma$-bis-sulfomethyl) Polymyxin E1. However, only a slight, but not significant, increase in urine KIM-1 levels was observed:

TABLE 2

| Urinary KIM-1 concentrations after 5 doses. | | |
|---|---|---|
| Treatment | Mouse id | KIM-1 (pg/ml) |
| A mixture comprising 93% mono (N$^\gamma$-bis-sulfomethyl) Polymyxin E1 25 mg/kg | 31 | 5400 |
| | 32 | 4700 |
| | 33 | 1600 |
| | 34 | 9500 |
| | 35 | 7350 |
| A mixture comprising 93% mono (N$^\gamma$-bis-sulfomethyl) Polymyxin E1 30 mg/kg | 36 | 6800 |
| | 37 | 3200 |
| | 38 | 8900 |
| | 40 | 5500 |
| CMS 32 mg/kg | 41 | 12700 |
| | 42 | 4350 |
| | 43 | 1950 |
| | 44 | 3800 |
| | 45 | 3800 |
| Gentamicin 80 mg/kg | 46 | 12850 |
| | 47 | 5900 |
| | 48 | 5750 |
| Vehicle | 51 | 6950 |
| | 52 | 5400 |
| | 54 | 2500 |

Example 6: In Vivo Activity of Mono Bis-Sulfomethylated Polymyxin E1

A mouse model with pulmonary infections of *Pseudomonas aeruginosa* (strain PAX11045) were treated with peritoneal administration of Polymyxin E1, CMS E1 and mono bis-sulfomethylated Polymyxin E1. CFU is the calculated number of colony forming units in the lung tissue after 22 hours except for the non-treatment group of mice. The clinical scoring is based on observations at the respective time points, as shown in table 3:

TABLE 3

| Treatment | log10 CFU lung | mean log10 CFU | Clinical score at T = 19 | Clinical score at T = 22 |
|---|---|---|---|---|
| None T = 4 | 6.00 | 6.10 | | |
| | 6.08 | | | |
| | 6.06 | | | |
| | 6.19 | | | |
| | 6.15 | | | |
| Polymyxin-E1 (dose: 10 mg/kg) | 5.65 | 4.43 | 3 | 4 |
| | 4.08 | | 2 | 2 |
| | 6.06 | | 3 | 4 |
| | 4.05 | | 3 | 3 |
| | 3.78 | | 3 | 3 |
| | 3.70 | | 3 | 3 |
| | 3.72 | | 3 | 3 |
| A mixture comprising mono (N$_\gamma$-bis-sulfomethyl) Polymyxin E1 (dose: 51 mg/kg) | 6.67 | 5.60 | 4 | |
| | 7.17 | | 4 | |
| | 6.13 | | 4 | |
| | 5.14 | | 3 | 3 |
| | 4.63 | | 3 | 3 |
| | 3.83 | | 3 | 3 |
| CMS E1 (dose: 41 mg/kg) | 3.95 | 4.53 | 2 | 2 |
| | 5.40 | | 4 | |
| | 3.98 | | 3 | 3 |
| | 4.60 | | 3 | 3 |
| | 4.65 | | 3 | 3 |
| | 4.60 | | 3 | 3 |

TABLE 3-continued

| Treatment | log10 CFU lung | mean log10 CFU | Clinical score at T = 19 | Clinical score at T = 22 |
|---|---|---|---|---|
| Vehicle | 7.05 | 6.80 | 3 | 5 |
| | 7.15 | | 3 | 5 |
| | 7.13 | | 3 | 5 |
| | 6.35 | | 3 | 4 |
| | 6.57 | | 3 | 4 |
| | 6.05 | | 3 | 4 |
| | 7.30 | | 3 | 4 |

| | |
|---|---|
| Score 0 | healthy |
| Score 1 | minor clinical signs of infection and inflammation like piloerection in the skin, distress and social withdrawal |
| Score 2 | moderate signs of infection like changed body position, changes in pattern of movement, lack of curiosity or changed activity. |
| Score 3 | severe signs of infection like stiff movements, forced ventilation, |
| Score 4 | severe pain, mouse was sacrificed immediately to minimize suffering |
| Score 5 | The mouse was dead |

The invention claimed is:
1. A polymyxin represented by formula (I):

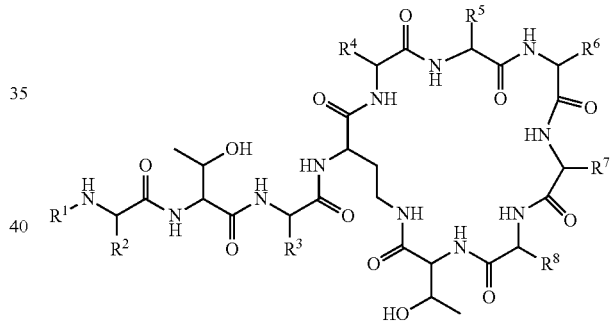

(I)

wherein
R$^1$ is an aliphatic linear or branched C$_6$-C$_{10}$ acyl group, or

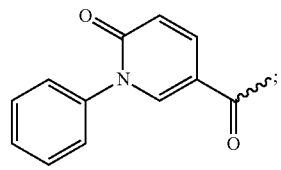

R$^5$ is —CH(CH$_3$)$_2$, —CH$_2$CH(CH$_3$)$_2$, —CH(CH$_3$)CH$_2$CH$_3$, or —CH$_2$C$_6$H$_5$;
R$^6$ is —CH(CH$_3$)$_2$, —CH$_2$CH(CH$_3$)$_2$, or —CH(CH$_3$)CH$_2$CH$_3$;
each of R$^2$, R$^3$, R$^4$, R$^7$ and R$^8$ is either —(CH$_2$)$_x$CH$_2$NH$_2$ or —(CH$_2$)$_x$CH$_2$N(CH$_2$SO$_3$M)$_2$;
wherein x is 0 or 1;
wherein M is a cation; and
wherein one of R$^2$, R$^3$, R$^4$, R$^7$ and R$^8$ is —(CH$_2$)$_x$CH$_2$N(CH$_2$SO$_3$M)$_2$, and the remaining four of R$^2$, R$^3$, R$^4$, R$^7$ and R$^8$ are —(CH$_2$)$_x$CH$_2$NH$_2$.

2. The polymyxin of claim 1, wherein $R^1$ is an aliphatic linear or branched $C_6$-$C_{10}$ acyl group.

3. The polymyxin of claim 2, wherein $R^1$ is heptanoyl, 6-methylheptanoyl, octanoyl, (S)-6-methyloctanoyl, 3-hydroxy-6-methyloctanoyl, 7-methyloctanoyl, nonanoyl, 8-methylnonanoyl or decanoyl.

4. The polymyxin of claim 1, wherein M is a pharmaceutically acceptable monovalent cation.

5. A composition comprising more than 50% as measured by HPLC of the polymyxin of claim 1.

6. A composition comprising more than 80% as measured by HPLC of the polymyxin of claim 1.

7. A composition comprising more than 90% as measured by HPLC of the polymyxin of claim 1.

8. A method of treating an infection caused by a Gram-negative bacterium, comprising contacting the bacterium with the polymixin of claim 1.

* * * * *